United States Patent
Titus et al.

(10) Patent No.: US 6,942,794 B2
(45) Date of Patent: Sep. 13, 2005

(54) HIGH VELOCITY CHROMATOGRAPHY COLUMN FLOW DISTRIBUTOR

(75) Inventors: Michael Titus, Ayer, MA (US); Aaron Noyes, Somerville, MA (US); Ian Rayner, Waltham, MA (US); Chris Antoniou, Chelmsford, MA (US)

(73) Assignee: Millipore Corporation, Billerica, MA (US)

( * ) Notice: Subject to any disclaimer, the term of this patent is extended or adjusted under 35 U.S.C. 154(b) by 0 days.

(21) Appl. No.: 10/779,995

(22) Filed: Feb. 17, 2004

(65) Prior Publication Data

US 2004/0184957 A1 Sep. 23, 2004

Related U.S. Application Data

(60) Provisional application No. 60/456,720, filed on Mar. 21, 2003.

(51) Int. Cl.$^7$ .............................................. B01D 15/08
(52) U.S. Cl. .................... 210/198.2; 210/456; 210/656; 96/107
(58) Field of Search ................................ 210/635, 656, 210/659, 198.2, 198.3, 456; 96/101, 107

(56) References Cited

U.S. PATENT DOCUMENTS

| | | | | |
|---|---|---|---|---|
| 4,557,830 A | * | 12/1985 | Onitsuka et al. ......... | 210/198.2 |
| 4,582,608 A | * | 4/1986 | Ritacco ..................... | 210/656 |
| 4,737,292 A | * | 4/1988 | Ritacco et al. ............. | 210/656 |
| 4,891,133 A | * | 1/1990 | Colvin, Jr. ................ | 210/198.2 |
| 4,894,152 A | | 1/1990 | Colvin, Jr. et al. | |
| 5,141,635 A | * | 8/1992 | LePlang et al. .......... | 210/198.2 |
| 5,167,810 A | * | 12/1992 | Vassarotti et al. ....... | 210/198.2 |
| 5,324,426 A | * | 6/1994 | Joseph et al. ............ | 210/198.2 |
| 5,423,982 A | | 6/1995 | Jungbauer et al. | |
| 6,139,732 A | | 10/2000 | Pelletier | |
| 6,224,760 B1 | | 5/2001 | Davies et al. | |

FOREIGN PATENT DOCUMENTS

EP                 476996               3/1992

* cited by examiner

Primary Examiner—Ernest G. Therkorn
(74) Attorney, Agent, or Firm—John Dana Hubbard

(57) ABSTRACT

The present invention is a flow distributor and integral bed support for a chromatography column. The flow distributor has an outlet extending through it and a bottom face across which is secured a bed support. The bottom face has a series of ribs extending radially outward from a center portion of the face. The bed support is secured to the flow distributor about its outer periphery and this amount of available surface area of the flow distributor and/or face that is used to secure the bed support is less than about 10%. A distribution disk is arranged over the inlet and extends across from about 1 to about 30% of the flow distributor's surface area, ending just short of the inner edge of the ribs closest to the center point of the flow distributor face. This disk is mounted on two or more legs so as to be of substantially the same height as the ribs. The disk projects the fluid flow in a 360° radial distribution without any noticeable partitioning. The flow distributor allows one to run the column at higher velocities up to 1500 cm/hour while maintaining its integrity and a standard flow across the flow distributor and while having a low-pressure drop across the column.

11 Claims, 3 Drawing Sheets

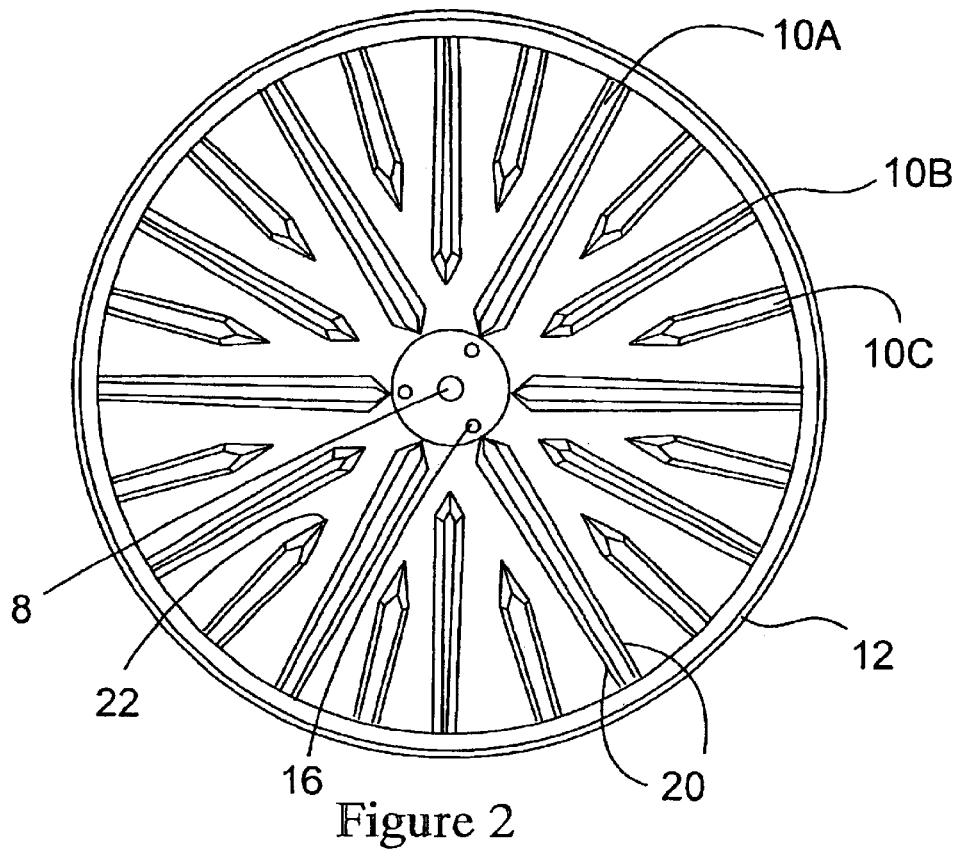
Figure 2
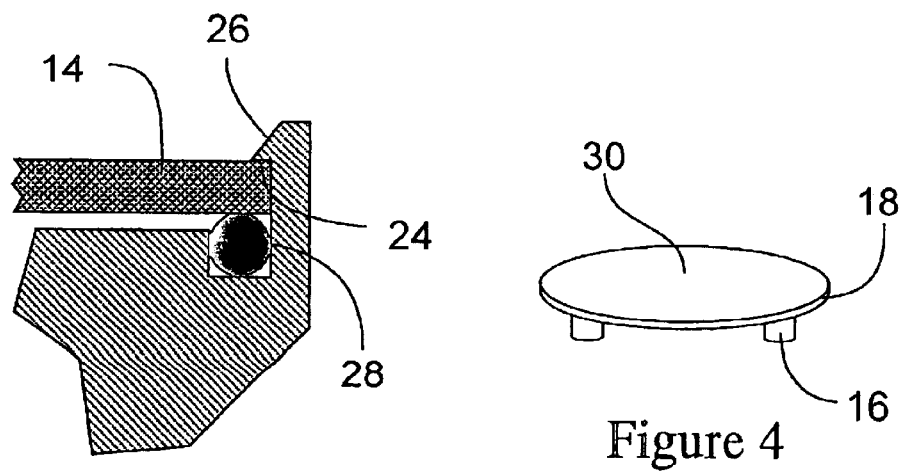
Figure 3
Figure 4

HIGH VELOCITY CHROMATOGRAPHY COLUMN FLOW DISTRIBUTOR

REFERENCE TO RELATED APPLICATIONS

This application seek priority from the provisional application No. 60/456,720 filed Mar. 21, 2003.

The present invention relates to a flow distributor for a chromatography column. More particularly it relates to a flow distributor for a chromatography column that has a high ratio of exposed distributor surface to the packed bed and is capable of withstanding high velocity flows with minimal pressure drop.

BACKGROUND OF THE INVENTION

Chromatography columns are typically formed of three main components, a body, a fixed bottom plate, and a movable top plate. The body is typically a hollow cylinder made of glass, acrylic or stainless steel. The bottom plate closes off the bottom of the body and typically has a screen and flow collector across its inner surface to collect fluid that passes through the column without disturbing the media that is also in the column. The bottom plate also has an outlet below the screen for the removal of the-fluid that has passed through the column.

The movable top plate, or flow distributor fits within the body and can move to a desired position above or on top of the media in the column. It too has a screen, commonly called a bed support across its face that is closest to the media, or bed. An inlet to the column is also formed through the top plate opening above the bed support into a space created between the face of the flow distributor and the bed support. The fluid then flows radially outward from the inlet and ideally passes uniformly through the bed support into the chromatography bed.

The flow direction can be reversed in most chromatography column designs, flowing through the bottom plate and exiting the top plate. Reversing the flow direction switches the utility of the top and bottom plates.

Most flow distributors contain a series of radial ribs on their face that help support the bed support and also help to spread the fluid outwardly in an even fashion across the face of the plate.

In practice, this design has several disadvantages.

As the inlet is typically centered on the face of the plate, there is a preference for the fluid to flow straight through the bed support directly below the inlet. This leads to non-uniform flow which adversely affects the performance of the column. At all but the slower velocities, this can cause the media below the inlet to be displaced creating a void in the bed which is designed to be uniform in cross section.

Current designs also use a large area of the peripheral edge to seal the bed support to the flow distributor. More than 10%, often more than 15% of the surface area of the top plate is consumed in this task. This limits the ability of the device to have even flow across its entire bed as the outer 10–15% of the bed doesn't receive direct flow. Limiting the surface area of the top plate adversely affects the column's performance while operating in the reverse flow direction.

Some columns use plastic bed supports, such as sintered polyethylene, but these incur other problems. One major problem with plastics is their inability to wet out, causing one to remove the air trapped in the pores before running the column. Likewise, any air that becomes entrapped in the bed during use is difficult to remove, as the plastic does not easily pass it through its structure. Another major problem with using plastic bed supports with the flow distributor is that they cannot and are not used on production size or large scale pilot chromatography columns without adding supports to the flow distributor which are obstructive to the flow distribution and may not be cleanable. This means that one cannot use the same design of flow distributor/bed supporting pilot and process scale applications and therefore the two designs will not be scalable thereby wasting time and money developing a separate protocol for the system.

Another disadvantage is that all of these effects are exacerbated at higher velocities. Additionally, the conventional design causes a high-pressure drop through the column at higher(greater than 100 cm/hr) velocities. High-pressure drops through the column can limit the velocity or alternatively the bed height at which the column can be safely operated.

Moreover, despite the large area used to secure the bed support to the flow distributor, at higher velocities, these bed supports have been known to detach from the flow distributor, especially plastic bed supports, or to bow outward, again creating a flow discontinuity.

One approach has been to secure the bed support at its center by a bolt that is screwed into the flow distributor. This has done little to solve the problems and creates another discontinuity in the bed as well as problems with the cleanability of the design.

In the Vantage® columns, available from Millipore Corporation of Billerica, Mass., a distribution disk has been formed so that its outer edge is mated with the inner portions of the ribs. This disk is permanently attached to the ribs.

It provides for a better flow distribution in that it reduces channeling and preferential flow down the center of the column bed. However, as it is sealed to the ribs, one now forms a series of quadrants through which fluid is divided and distributed. It still uses greater than 10% of the surface area of the flow distribution face to attach the bed support and it still cannot handle higher velocities.

What is needed is a better flow distributor design that has good flow distribution characteristics while acting as a flow distribution point or a collection point, less than about 10% of the available surface used to seal the bed support to the flow distributor and which is able to handle higher velocities with little pressure drop and without bowing or detaching the bed support.

SUMMARY OF THE INVENTION

The present invention is a flow distributor and integral bed support for a chromatography column. The flow distributor has an outlet extending through it and a bottom face across which is secured a bed support. The bottom face has a series of ribs extending radially outward from a center portion of the face. The bed support is secured to the flow distributor about its outer periphery and this amount of available surface area of the flow distributor and/or face that is used to secure the bed support is less than about 10%.

A distribution disk is arranged over the inlet and extends across from about 1 to about 30% of the flow distributor's surface area, ending just short of the inner edge of the ribs closest to the center point of the flow distributor face. This disk is mounted on two or more legs so as to be of substantially the same height as the ribs. The disk projects the fluid flow in a 360° radial distribution without any noticeable partitioning.

The flow distributor allows one to run the column at higher velocities up to 1500 cm/hour while maintaining its integrity and a standard flow across the flow distributor and while having a low-pressure drop across the column.

IN THE DRAWINGS

FIG. 2 shows bottom up planar view of the top plate and flow disk.

FIG. 3 shows a close up cross sectional view of the flow distributor and top plate edge.

FIG. 4 shows a perspective view of the flow disk.

DETAILED DESCRIPTION OF THE INVENTION

Figure 1:
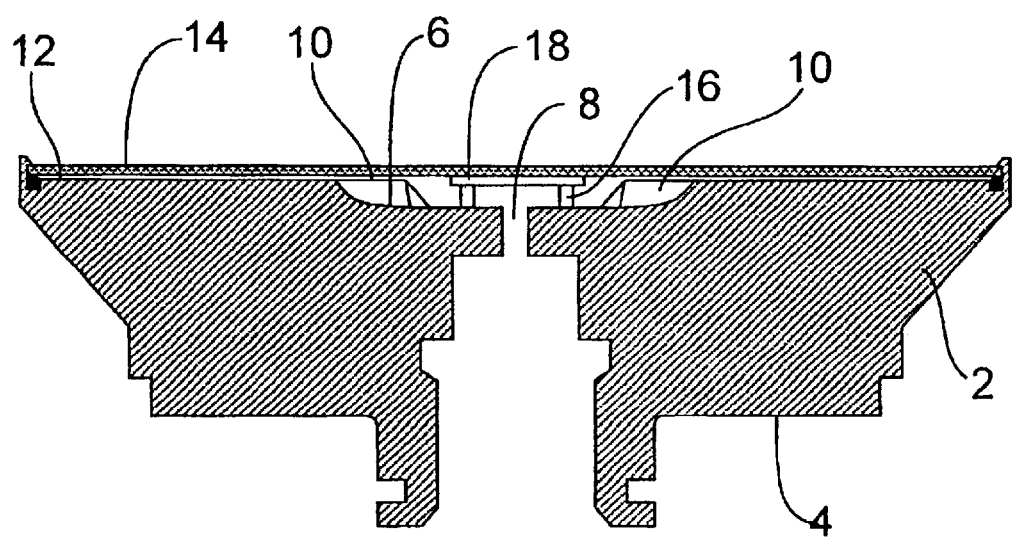
FIG. 1 shows a first embodiment of the invention in cross sectional view.

FIG. 1 shows a flow distributor according to one embodiment of the present invention. The flow distributor 2 has an upper surface 4 and a lower surface 6 (which faces into the chromatography column, not shown) which moves the flow distributor 2 into and out of the column see U.S. Pat. No. 6,139.732 and EP 476 996 A2 for examples of adjuster devices.

The inlet 8 extends through the flow distributor 2 to the bottom surface 6. As shown, the bottom surface 6 contains a series of ribs 10 that extend radially outward from an area adjacent the center of the bottom surface 6 toward the outer peripheral edge 12 of the bottom surface 6.

A bed support 14 is mounted to bottom surface 6 and held at the outer peripheral edge 12 of the top plate 2.

Located above the inlet 8 and secured to the bottom surface 6 by two or more legs 16 is a distributor disk 18.

FIG. 2 shows the bottom surface of the flow distributor with the distributor disk in place and the bed support yet to be attached.

As shown, there is a series of different sized ribs (10A, 10B, 10C). In this instance, three series of ribs equally spaced apart from each other. Series 10A is the longest ribs and extend from a point adjacent to the outer edge of the disk to the outer peripheral edge of the bottom surface. As shown, this series is comprised of 6 ribs, spaced 60° from each other. The distance of the leading edge of this series of ribs A from the center of the surface is about 19% of the radius of the surface. It may be more or less as is desired or required. Typically, it ranges from about 10% to 30% of the radius of the surface, preferably from about 16% to about 22%. This distance ensures the uniformity of the radial distribution by decreasing the obstruction caused by the ribs at the inlet.

Series 10B ribs are shorter in length than those of Series 10A starting farther away from the center of the inlet than the 10A ribs. They are also, as shown, equal in number to those of series 10A and are equally spaced apart from each other (in this embodiment by 60°) and the series 10A ribs.

The series 10C ribs are the shortest, in this embodiment about ½ the length of the series 10A ribs extending from the outer peripheral edge 12 toward the center of the inlet. These ribs are shown to be twelve in number, equally spaced from each other and each adjacent series 10A, 10B rib.

Other rib designs may also be used so long as the flow distribution is uniform and the bed support is uniformly supported. It is meant to cover these embodiments as well in this present invention. The ribs as shown have tapered side edges 20 and terminate at a tapered tip 22 of the point of the rib 10 closest to the center of the inlet. This allows for optimum flow characteristics and is industry-accepted practice. Other rib designs include rounded ribs and even non-tapered ribs may be used so long as they provide adequate flow distribution and support.

FIG. 3 shows one embodiment of the sealing mechanism in detail.

As shown, the outer edge 12 of the flow distributor 2 on its bottom surface 6 has an undercut 24 into which the bed support 14 is placed. The upper arm 26 of the undercut 24 keeps the bed support in place, preventing it from separating during use at higher velocities. Also shown is an optional gasket 28 in the undercut to prevent any dead or non-flow areas. In many applications this gasket may be unnecessary.

The undercut 21 and arm 26 can be molded as an integral piece of the flow distributor 2. Alternatively, the upper arm 26 can be molded in a more vertical position and, after inserting the bed support into the undercut 24; the upper arm 26 is pushed or crimped downward toward the flow distributor 14.

In another embodiment (not shown) the upper arm and outer edge portion 12 of the flow distributor 2 are formed separately and then attached to the top plate 2 after positioning the bed support 14 in place. Glues, sonic welding, thermal bonding, mated threads and screws and the like may be used to attach the two pieces together.

The length of the upper arm 26 should be as small as possible so as to maximize the available active surface of the flow distributor. Preferably it is such that the ratio of active flow distributor surface area to the entire surface area of the column bed below it is at least 0.9, preferably from about 0.9 to about 0.95.

FIG. 4 shows the disk distributor of FIGS. 1 and 2 in more detail. As shown, it is formed of a circular top portion 30 and two or more legs 16. In this instance, three legs 16 are shown. Three legs 16 is a preferred embodiment as it provides maximum stability with minimal flow disruption. The disk 18 can be from about 1 to about 30% of the bottom surface's total surface area. Preferably, it is from about 1% to about 4% of the total area and more preferably it is from about 2% to about 3% of the total area. In one embodiment, it comprises 2.4% of the total surface area.

The legs 16 should be of a height such that the top surface 30 of the disk is substantially at the same height as the adjacent ribs (not shown in FIG. 4 but see FIG. 1). This is preferred as it makes the surface of the flow distributor 14 as planar as possible, thus eliminating any discontinuities in the flow of the fluid or the profile of the chromatography bed.

The disk 18 and its legs 16 are designed to minimize the obstruction to the 360° radial flow distribution.

Depending upon how the disk is attached to the bottom surface, the legs 16 may be longer than the actual finished height. For example, where the legs are fitted into a recess in the bottom surface and glued, thermally bonded, friction fit, or welded in place, the legs should be of a length to allow them to fully seal in the recesses and bring the top surface 30 of the disk 18 into substantially parallel alignment with the top surfaces of the ribs 10.

In one preferred embodiment, the legs 16 are cylindrical and have a diameter of about 1 mm.

The legs 16 should also preferably be arranged around the disk so as to be in line with the rays of the closest ribs. In this way, flow disruption is again minimized.

The disk 18 can be made of metal such as stainless steel (either machined or cast) or plastic (either machined or cast)

such as polyethylene, polypropylene, PA, PEEK resin, PTFE resin, perfluorinated thermoplastic resins such as PFA, MFA and FEP resins and acrylics. It is preferred that it be made of the same material as the flow distributor.

The bed support may be made of any of the conventional materials used in chromatography columns such as metal, glass and plastic.

One preferred bed support is made of stainless steel with a series of pores formed through it for fluid flow into the column. Metal, such as stainless steel is preferred in the present invention as it does not present wetting out issues and is extremely resistant to pressure and higher velocity flow rates while maintaining a standard porosity across the bed support.

The support can be formed of one or more layers of metal screen or cloth, typically of two or more layers with different sized mesh openings as is commonly used in the chromatography industry today. The screens or cloth are typically formed of a woven metal fibers and may be arranged in a warp/weft pattern that is perpendicular to each other or at some other angle to each other. Sintered porous metal may also be used. Likewise, a solid metal plate having a series of holes formed through it may also be used to advantage in this invention. The pores of the solid plate design are preferably formed by machining, stamping, chemical etching, water jet cutting, or laser drilling as they provide the most uniform distribution of holes available.

Plastic bed supports are also useful in the present invention. The holes may be made from sintered porous plastics, or machine etched, or laser drilled, or woven, or molded, or cast. Likewise, one or more layers of plastic screens and/or fabrics may be used as well.

In some instances, glass or ceramics may be used to form the bed support. The holes may be formed by using a sintered porous glass or ceramics or they may be formed by machining, etching or laser drilling.

Likewise, the flow distributor may be formed of a metal, such as stainless steel or anodized aluminum, a plastic such as polyethylene or polypropylene, or a composite material such as carbon fiber, epoxy, graphite, ceramic or glass fiber filled plastic.

Preferably, it is made of stainless steel or polypropylene.

The ribs 10 may be formed by machining the bottom surface of the flow distributor or when the flow distributor is cast, the ribs may be formed as an integral feature of that casting.

The disk distributor may also be made of metal such as stainless steel, plastics such as polyethylene or a ceramic or composite. It must be substantially non-porous to ensure good flow distribution and have sufficient strength to withstand the higher flow velocities. Stainless steel and polypropylene are preferred.

Figure 5:
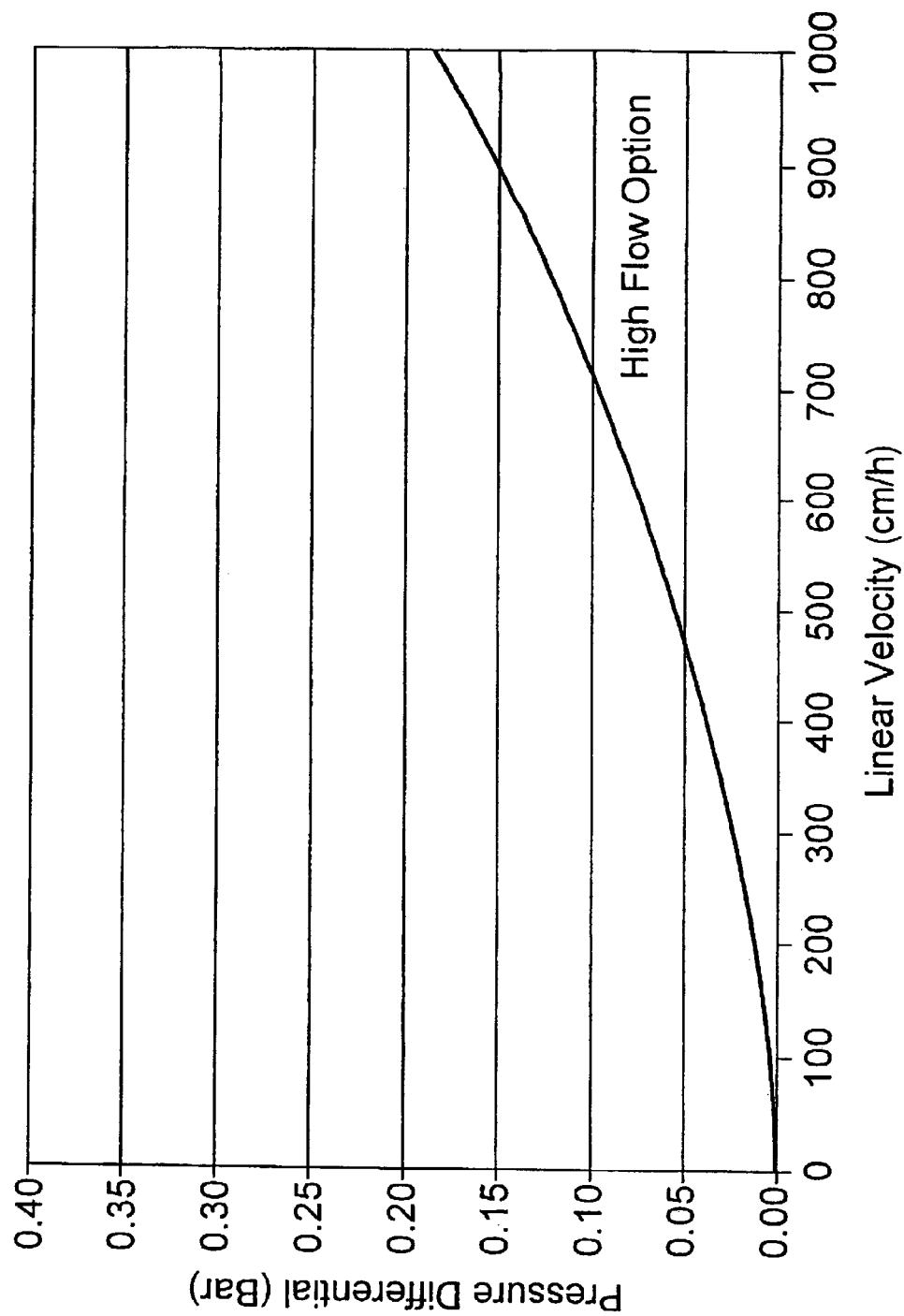
FIG. 5 shows a graphical representation of the pressure flow curve for a column using the flow distributor of the present invention.

FIG. 5 shows a pressure flow curve derived for a column using the flow distributor of the present invention. A 100 mm diameter column having a fixed bottom plate and a movable flow distributor as the top plate was used. The flow distributor was positioned 20 cm above the bottom of the column and run with water at flow rates of from 0 to 1000 cm/hour (no media was added). Pressure of the water was measured at the inlet to and outlet from the column. The resulting curve was plotted from the data obtained.

This curve demonstrates that the flow distributor of the present invention has a minimal pressure drop even at high velocities.

What we claim:

1. A flow distributor for a chromatography column comprising a flow distributor having a top face and a bottom face, an inlet extending through it and a bottom face across which is secured a bed support, the bottom face has one or more series of ribs extending radially outward from a center portion of the bottom face, a bed support is secured to the flow distributor adjacent its bottom face about its outer periphery, a distribution disk is arranged over the inlet and extending across from about 1 to about 30% of the flow distributor's bottom face area, ending just short of an inner edge of the one or more series of ribs closest to a center point of the inlet, the disk being mounted on two or more legs so as to be of substantially the same height as the ribs, and wherein the disk projects fluid flow from the inlet in a 360° radial distribution without any noticeable partitioning.

2. The flow distributor of claim 1 wherein the flow distributor allows a column to run velocities up to 1500 cm/hour while maintaining its integrity and a standard flow across the flow distributor and while having a low-pressure drop across the column.

3. The flow distributor of claim 1 wherein the ratio of active flow distributor surface area to the entire surface area of the column bed below it is at least 0.9.

4. The flow distributor of claim 1 wherein the disk is from about 1% to about 4% of the bottom face's total surface area.

5. The flow distributor of claim 1 wherein the disk is from about 2% to about 3% of the bottom face's total surface area.

6. The flow distributor of claim 1 wherein the disk is from about 2.4% of the bottom face's total surface area.

7. The flow distributor of claim 1 wherein the one or more series of ribs have a leading edge closest to a center of the surface and the leading edge is spaced from the center of the surface by a distance about 19% that of the radius of the surface.

8. The flow distributor of claim 1 wherein the one or more series of ribs have a leading edge closest to a center of the surface and the leading edge is spaced from the center of the surface by a distance from about 10% to about 30% of the radius of the surface.

9. The flow distributor of claim 1 wherein the one or more series of ribs have a leading edge closest to a center of the surface and the leading edge is spaced from the center of the surface by a distance from about 16% to about 22% of the radius of the surface.

10. The flow distributor of claim 1 wherein the amount of surface area of the bottom face of the flow distributor that is used to secure the bed support is less than about 10%.

11. The flow distributor of claim 1 wherein the ratio of active flow distributor surface area to the entire surface area of the column bed it is about 0.9 to about 0.95.

* * * * *